United States Patent
Hashmi et al.

(10) Patent No.: US 7,501,266 B2
(45) Date of Patent: Mar. 10, 2009

(54) DIFFERENTIATING HOMOZYGOUS, HETEROZYGOUS AND WILD-TYPE ALLELES USING A MULTIPLEXED HYBRIDIZATION-MEDIATED ASSAY

(75) Inventors: Ghazala Hashmi, Holmdel, NJ (US); Michael Seul, Fanwood, NJ (US)

(73) Assignee: BioArray Solutions, Ltd., Warren, NJ (US)

( * ) Notice: Subject to any disclaimer, the term of this patent is extended or adjusted under 35 U.S.C. 154(b) by 415 days.

(21) Appl. No.: 11/439,697

(22) Filed: May 23, 2006

(65) Prior Publication Data

US 2006/0228744 A1    Oct. 12, 2006

Related U.S. Application Data

(63) Continuation of application No. 10/847,046, filed on May 17, 2004.

(60) Provisional application No. 60/470,806, filed on May 15, 2003.

(51) Int. Cl.
   *C12Q 1/68*    (2006.01)
   *C12P 19/34*   (2006.01)
   *C12N 9/00*    (2006.01)
   *G01N 33/53*   (2006.01)
   *C07H 21/04*   (2006.01)

(52) U.S. Cl. .......... 435/91.2; 435/6; 435/91.1; 435/183; 436/800; 536/23.1; 536/24.3; 536/24.33

(58) Field of Classification Search .......... 435/6, 435/91.1, 91.2, 183, 287.2; 536/23.1, 24.31, 536/24.32, 24.33
   See application file for complete search history.

(56) References Cited

U.S. PATENT DOCUMENTS

| | | | | |
|---|---|---|---|---|
| 5,200,313 | A | * | 4/1993 | Carrico .................... 435/6 |
| 5,308,749 | A | | 5/1994 | Sutton et al. |
| 5,474,796 | A | | 12/1995 | Brennan |
| 5,604,099 | A | | 2/1997 | Erlich et al. |
| 6,124,092 | A | | 9/2000 | O'Neill et al. |
| 6,480,791 | B1 | | 11/2002 | Strathmann |
| 6,534,293 | B1 | | 3/2003 | Barany et al. |
| 2002/0119455 | A1 | * | 8/2002 | Chan ....................... 435/6 |
| 2006/0286570 | A1 | * | 12/2006 | Rowlen et al. ............ 435/6 |
| 2007/0009954 | A1 | * | 1/2007 | Wang et al. ............... 435/6 |
| 2007/0031829 | A1 | * | 2/2007 | Yasuno et al. ............ 435/6 |
| 2007/0042400 | A1 | * | 2/2007 | Choi et al. ............... 435/6 |
| 2007/0042419 | A1 | * | 2/2007 | Barany et al. ............. 435/6 |

OTHER PUBLICATIONS

Zhang et al., Bioinforrmatics, vol. 19, No. 1, 2003, pp. 14-21.*

* cited by examiner

*Primary Examiner*—Bradley L Sisson
(74) *Attorney, Agent, or Firm*—Eric P. Mirabel

(57) ABSTRACT

Described are methods of assay design and assay image correction, useful for multiplexed genetic screening for mutations and polymorphisms, including CF-related mutants and polymorphs, using an array of probe pairs (in one aspect, where one member is complementary to a particular mutant or polymorphic allele and the other member is complementary to a corresponding wild type allele), with probes bound to encoded particles (e.g., beads) wherein the encoding allows identification of the attached probe. The methods relate to avoiding cross-hybridization by selection of probes and amplicons, as well as separation of reactions of certain probes and amplicons where a homology threshold is exceeded. Methods of correcting a fluorescent image using a background map, where the particles also contain an optical encoding system, are also disclosed.

4 Claims, 2 Drawing Sheets

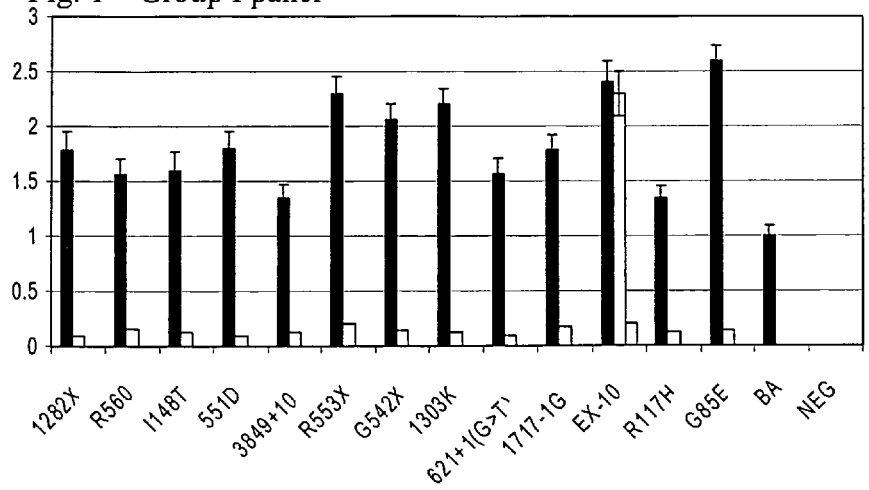
Fig. 1 – Group I panel
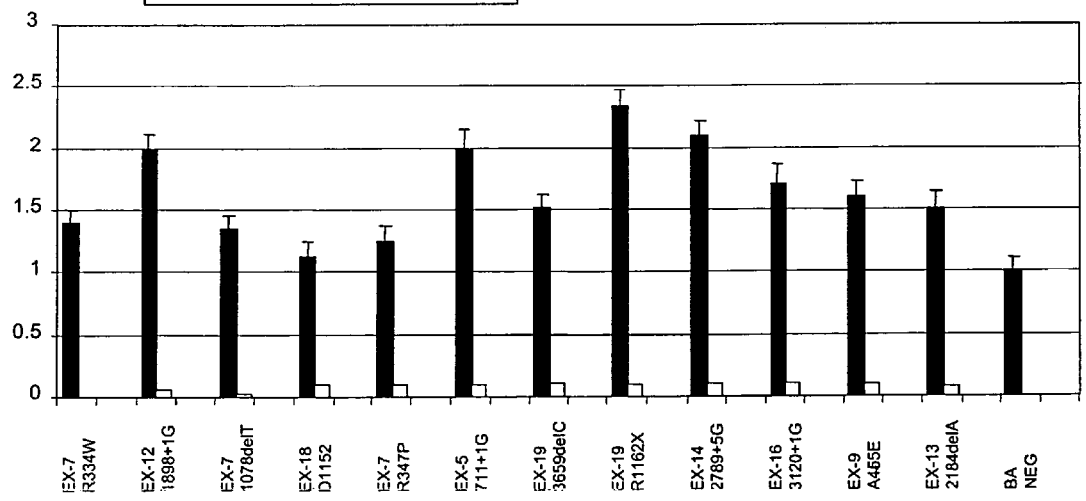
Fig. 2 – Group II Panel

SEQUENCE LISTING

<160> NUMBER OF SEQ ID NOS: 83

<210> SEQ ID NO 1
<211> LENGTH: 19
<212> TYPE: DNA

```
<213> ORGANISM: Artificial Sequence
<220> FEATURE:
<223> OTHER INFORMATION: artificial primer

<400> SEQUENCE: 1
gtcaagccgt gttctagat                                                  19

<210> SEQ ID NO 2
<211> LENGTH: 23
<212> TYPE: DNA
<213> ORGANISM: Artificial Sequence
<220> FEATURE:
<223> OTHER INFORMATION: artificial primer

<400> SEQUENCE: 2
gttgtataat ttataacaat agt                                             23

<210> SEQ ID NO 3
<211> LENGTH: 20
<212> TYPE: DNA
<213> ORGANISM: Artificial Sequence
<220> FEATURE:
<223> OTHER INFORMATION: artificial primer

<400> SEQUENCE: 3
acttcaatag ctcagccttc                                                 20

<210> SEQ ID NO 4
<211> LENGTH: 23
<212> TYPE: DNA
<213> ORGANISM: Artificial Sequence
<220> FEATURE:
<223> OTHER INFORMATION: artificial primer

<400> SEQUENCE: 4
tatggtacat tacctgtatt ttg                                             23

<210> SEQ ID NO 5
<211> LENGTH: 18
<212> TYPE: DNA
<213> ORGANISM: Artificial Sequence
<220> FEATURE:
<223> OTHER INFORMATION: artificial primer

<400> SEQUENCE: 5
tggtgacagc ctcttctt                                                   18

<210> SEQ ID NO 6
<211> LENGTH: 20
<212> TYPE: DNA
<213> ORGANISM: Artificial Sequence
<220> FEATURE:
<223> OTHER INFORMATION: artificial primer

<400> SEQUENCE: 6
gaactacctt gcctgctcca                                                 20

<210> SEQ ID NO 7
<211> LENGTH: 21
<212> TYPE: DNA
<213> ORGANISM: Artificial Sequence
<220> FEATURE:
<223> OTHER INFORMATION: artificial primer

<400> SEQUENCE: 7 tctcctttg gatacctaga t                                                21
```

<210> SEQ ID NO 8
<211> LENGTH: 21
<212> TYPE: DNA
<213> ORGANISM: Artificial Sequence
<220> FEATURE:
<223> OTHER INFORMATION: artificial primer

<400> SEQUENCE: 8
tgagcattat aagtaaggta t                                              21

<210> SEQ ID NO 9
<211> LENGTH: 21
<212> TYPE: DNA
<213> ORGANISM: Artificial Sequence
<220> FEATURE:
<223> OTHER INFORMATION: artificial primer

<400> SEQUENCE: 9
aggtagcagc tatttttatg g                                              21

<210> SEQ ID NO 10
<211> LENGTH: 18
<212> TYPE: DNA
<213> ORGANISM: Artificial Sequence
<220> FEATURE:
<223> OTHER INFORMATION: artificial primer

<400> SEQUENCE: 10
atctggtact aaggacag                                                  18

<210> SEQ ID NO 11
<211> LENGTH: 20
<212> TYPE: DNA
<213> ORGANISM: Artificial Sequence
<220> FEATURE:
<223> OTHER INFORMATION: artificial primer

<400> SEQUENCE: 11
tctttggttg tgctgtggct                                                20

<210> SEQ ID NO 12
<211> LENGTH: 20
<212> TYPE: DNA
<213> ORGANISM: Artificial Sequence
<220> FEATURE:
<223> OTHER INFORMATION: artificial primer

<400> SEQUENCE: 12
acaatacata caaacatagt                                                20

<210> SEQ ID NO 13
<211> LENGTH: 21
<212> TYPE: DNA
<213> ORGANISM: Artificial Sequence
<220> FEATURE:
<223> OTHER INFORMATION: artificial primer

<400> SEQUENCE: 13
cttctgctta ccatatttga c                                              21

<210> SEQ ID NO 14
<211> LENGTH: 20
<212> TYPE: DNA
<213> ORGANISM: Artificial Sequence
<220> FEATURE:
<223> OTHER INFORMATION: artificial primer

```
<400> SEQUENCE: 14
taatacagac atacttaacg                                              20

<210> SEQ ID NO 15
<211> LENGTH: 20
<212> TYPE: DNA
<213> ORGANISM: Artificial Sequence
<220> FEATURE:
<223> OTHER INFORMATION: artificial primer

<400> SEQUENCE: 15
ggagaaggag aaggaagagt                                              20

<210> SEQ ID NO 16
<211> LENGTH: 21
<212> TYPE: DNA
<213> ORGANISM: Artificial Sequence
<220> FEATURE:
<223> OTHER INFORMATION: artificial primer

<400> SEQUENCE: 16
atctatgaga aggaaagaag a                                            21

<210> SEQ ID NO 17
<211> LENGTH: 20
<212> TYPE: DNA
<213> ORGANISM: Artificial Sequence
<220> FEATURE:
<223> OTHER INFORMATION: artificial primer

<400> SEQUENCE: 17
ggccaaatga ctgtcaaaga                                              20

<210> SEQ ID NO 18
<211> LENGTH: 20
<212> TYPE: DNA
<213> ORGANISM: Artificial Sequence
<220> FEATURE:
<223> OTHER INFORMATION: artificial primer

<400> SEQUENCE: 18
tgcttcaggc tactgggatt                                              20

<210> SEQ ID NO 19
<211> LENGTH: 20
<212> TYPE: DNA
<213> ORGANISM: Artificial Sequence
<220> FEATURE:
<223> OTHER INFORMATION: artificial primer

<400> SEQUENCE: 19
cggcgatgtt ttttctggag                                              20

<210> SEQ ID NO 20
<211> LENGTH: 20
<212> TYPE: DNA
<213> ORGANISM: Artificial Sequence
<220> FEATURE:
<223> OTHER INFORMATION: artificial primer

<400> SEQUENCE: 20
tacaaatgag atccttaccc                                              20
```

<210> SEQ ID NO 21
<211> LENGTH: 20
<212> TYPE: DNA
<213> ORGANISM: Artificial Sequence
<220> FEATURE:
<223> OTHER INFORMATION: artificial primer

<400> SEQUENCE: 21
agcttcctat gacccggata                                          20

<210> SEQ ID NO 22
<211> LENGTH: 20
<212> TYPE: DNA
<213> ORGANISM: Artificial Sequence
<220> FEATURE:
<223> OTHER INFORMATION: artificial primer

<400> SEQUENCE: 22
tgtgatgaag gccaaaaatg                                          20

<210> SEQ ID NO 23
<211> LENGTH: 20
<212> TYPE: DNA
<213> ORGANISM: Artificial Sequence
<220> FEATURE:
<223> OTHER INFORMATION: artificial primer

<400> SEQUENCE: 23
tgttctcagt tttcctggat                                          20

<210> SEQ ID NO 24
<211> LENGTH: 20
<212> TYPE: DNA
<213> ORGANISM: Artificial Sequence
<220> FEATURE:
<223> OTHER INFORMATION: artificial primer

<400> SEQUENCE: 24
ctcttctagt tggcatgctt                                          20

<210> SEQ ID NO 25
<211> LENGTH: 20
<212> TYPE: DNA
<213> ORGANISM: Artificial Sequence
<220> FEATURE:
<223> OTHER INFORMATION: artificial primer

<400> SEQUENCE: 25
cagattgagc atactaaaag                                          20

<210> SEQ ID NO 26
<211> LENGTH: 20
<212> TYPE: DNA
<213> ORGANISM: Artificial Sequence
<220> FEATURE:
<223> OTHER INFORMATION: artificial primer

<400> SEQUENCE: 26
acatgaatga catttacagc                                          20

<210> SEQ ID NO 27
<211> LENGTH: 21
<212> TYPE: DNA
<213> ORGANISM: Artificial Sequence
<220> FEATURE:
<223> OTHER INFORMATION: artificial primer

<400> SEQUENCE: 27
aatcattcag tgggtataag c                    21

<210> SEQ ID NO 28
<211> LENGTH: 21
<212> TYPE: DNA
<213> ORGANISM: Artificial Sequence
<220> FEATURE:
<223> OTHER INFORMATION: artificial primer

<400> SEQUENCE: 28
cctcctccct gagaatgttg g                    21

<210> SEQ ID NO 29
<211> LENGTH: 20
<212> TYPE: DNA
<213> ORGANISM: Artificial Sequence
<220> FEATURE:
<223> OTHER INFORMATION: artificial primer

<400> SEQUENCE: 29
ctggatcagg gaagagaagg                      20

<210> SEQ ID NO 30
<211> LENGTH: 20
<212> TYPE: DNA
<213> ORGANISM: Artificial Sequence
<220> FEATURE:
<223> OTHER INFORMATION: artificial primer

<400> SEQUENCE: 30 tcctttttgct cacctgtggt                     20

<210> SEQ ID NO 31
<211> LENGTH: 20
<212> TYPE: DNA
<213> ORGANISM: Artificial Sequence
<220> FEATURE:
<223> OTHER INFORMATION: artificial primer

<400> SEQUENCE: 31
tgatggtaag tacatgggtg                      20

<210> SEQ ID NO 32
<211> LENGTH: 20
<212> TYPE: DNA
<213> ORGANISM: Artificial Sequence
<220> FEATURE:
<223> OTHER INFORMATION: artificial primer

<400> SEQUENCE: 32
caaaagtacc tgttgctcca                      20

<210> SEQ ID NO 33
<211> LENGTH: 21
<212> TYPE: DNA
<213> ORGANISM: Artificial Sequence
<220> FEATURE:
<223> OTHER INFORMATION: artificial probe

<400> SEQUENCE: 33
atgttctatg gaatcttttt a                    21

```
<210> SEQ ID NO 34
<211> LENGTH: 21
<212> TYPE: DNA
<213> ORGANISM: Artificial Sequence
<220> FEATURE:
<223> OTHER INFORMATION: artificial probe

<400> SEQUENCE: 34
atgttctatg aaatctttt a                                              21

<210> SEQ ID NO 35
<211> LENGTH: 21
<212> TYPE: DNA
<213> ORGANISM: Artificial Sequence
<220> FEATURE:
<223> OTHER INFORMATION: artificial probe

<400> SEQUENCE: 35
tataagaagg taatacttcc t                                             21

<210> SEQ ID NO 36
<211> LENGTH: 21
<212> TYPE: DNA
<213> ORGANISM: Artificial Sequence
<220> FEATURE:
<223> OTHER INFORMATION: artificial probe

<400> SEQUENCE: 36
tataagaagt taatacttcc t                                             21

<210> SEQ ID NO 37
<211> LENGTH: 21
<212> TYPE: DNA
<213> ORGANISM: Artificial Sequence
<220> FEATURE:
<223> OTHER INFORMATION: artificial probe

<400> SEQUENCE: 37
cctcatcaca ttggaatgca g                                             21

<210> SEQ ID NO 38
<211> LENGTH: 21
<212> TYPE: DNA
<213> ORGANISM: Artificial Sequence
<220> FEATURE:
<223> OTHER INFORMATION: artificial probe

<400> SEQUENCE: 38
cctcatcaca ctggaatgca g                                             21

<210> SEQ ID NO 39
<211> LENGTH: 21
<212> TYPE: DNA
<213> ORGANISM: Artificial Sequence
<220> FEATURE:
<223> OTHER INFORMATION: artificial probe

<400> SEQUENCE: 39
caaggaggaa cgctctatcg c                                             21

<210> SEQ ID NO 40
<211> LENGTH: 21
<212> TYPE: DNA
<213> ORGANISM: Artificial Sequence
<220> FEATURE:
<223> OTHER INFORMATION: artificial probe
```

<400> SEQUENCE: 40
caaggaggaa cactctatcg c                                              21

<210> SEQ ID NO 41
<211> LENGTH: 21
<212> TYPE: DNA
<213> ORGANISM: Artificial Sequence
<220> FEATURE:
<223> OTHER INFORMATION: artificial probe

<400> SEQUENCE: 41
atgggtacat acttcatcaa a                                              21

<210> SEQ ID NO 42
<211> LENGTH: 21
<212> TYPE: DNA
<213> ORGANISM: Artificial Sequence
<220> FEATURE:
<223> OTHER INFORMATION: artificial probe

<400> SEQUENCE: 42
atgggtacat aattcatcaa a                                              21

<210> SEQ ID NO 43
<211> LENGTH: 21
<212> TYPE: DNA
<213> ORGANISM: Artificial Sequence
<220> FEATURE:
<223> OTHER INFORMATION: artificial probe

<400> SEQUENCE: 43
gaatattttc cggaggatga t                                              21

<210> SEQ ID NO 44
<211> LENGTH: 21
<212> TYPE: DNA
<213> ORGANISM: Artificial Sequence
<220> FEATURE:
<223> OTHER INFORMATION: artificial probe

<400> SEQUENCE: 44
gaatattttc cagaggatga t                                              21

<210> SEQ ID NO 45
<211> LENGTH: 21
<212> TYPE: DNA
<213> ORGANISM: Artificial Sequence
<220> FEATURE:
<223> OTHER INFORMATION: artificial probe

<400> SEQUENCE: 45
cattgttctg cgcatggcgg t                                              21

<210> SEQ ID NO 46
<211> LENGTH: 21
<212> TYPE: DNA
<213> ORGANISM: Artificial Sequence
<220> FEATURE:
<223> OTHER INFORMATION: artificial probe

<400> SEQUENCE: 46
cattgttctg cccatggcgg t                                              21

<210> SEQ ID NO 47
<211> LENGTH: 21
<212> TYPE: DNA
<213> ORGANISM: Artificial Sequence
<220> FEATURE:
<223> OTHER INFORMATION: artificial probe

<400> SEQUENCE: 47
ctcagggttc tttgtggtgt t                                     21

<210> SEQ ID NO 48
<211> LENGTH: 20
<212> TYPE: DNA
<213> ORGANISM: Artificial Sequence
<220> FEATURE:
<223> OTHER INFORMATION: artificial probe

<400> SEQUENCE: 48
ctcagggttc ttgtggtgtt                                       20

<210> SEQ ID NO 49
<211> LENGTH: 21
<212> TYPE: DNA
<213> ORGANISM: Artificial Sequence
<220> FEATURE:
<223> OTHER INFORMATION: Artificial Probe

<400> SEQUENCE: 49
acagttgttg gcggttgctg g                                     21

<210> SEQ ID NO 50
<211> LENGTH: 21
<212> TYPE: DNA
<213> ORGANISM: Artificial Sequence
<220> FEATURE:
<223> OTHER INFORMATION: Artificial Probe

<400> SEQUENCE: 50
acagttgttg gaggttgctg g                                     21

<210> SEQ ID NO 51
<211> LENGTH: 21
<212> TYPE: DNA
<213> ORGANISM: Artificial Sequence
<220> FEATURE:
<223> OTHER INFORMATION: Artificial Probe

<400> SEQUENCE: 51
aaagaaaata tcatctttgg t                                     21

<210> SEQ ID NO 52
<211> LENGTH: 20
<212> TYPE: DNA
<213> ORGANISM: Artificial Sequence
<220> FEATURE:
<223> OTHER INFORMATION: Artificial Probe

<400> SEQUENCE: 52
aaagaaaata tcattggtgt                                       20

<210> SEQ ID NO 53
<211> LENGTH: 20
<212> TYPE: DNA
<213> ORGANISM: Artificial Sequence
<220> FEATURE:
<223> OTHER INFORMATION: Artificial Probe

```
<400> SEQUENCE: 53
aaagaaaata tctttggtgt                                              20

<210> SEQ ID NO 54
<211> LENGTH: 22
<212> TYPE: DNA
<213> ORGANISM: Artificial Sequence
<220> FEATURE:
<223> OTHER INFORMATION: Artificial Probe

<400> SEQUENCE: 54
atatttgaaa ggtatgttct tt                                           22

<210> SEQ ID NO 55
<211> LENGTH: 22
<212> TYPE: DNA
<213> ORGANISM: Artificial Sequence
<220> FEATURE:
<223> OTHER INFORMATION: Artificial Probe

<400> SEQUENCE: 55
atatttgaaa gatatgttct tt                                           22

<210> SEQ ID NO 56
<211> LENGTH: 21
<212> TYPE: DNA
<213> ORGANISM: Artificial Sequence
<220> FEATURE:
<223> OTHER INFORMATION: Artificial Probe

<400> SEQUENCE: 56
gaaacaaaaa aacaatcttt t                                            21

<210> SEQ ID NO 57
<211> LENGTH: 20
<212> TYPE: DNA
<213> ORGANISM: Artificial Sequence
<220> FEATURE:
<223> OTHER INFORMATION: Artificial Probe

<400> SEQUENCE: 57
gaaacaaaaa acaatctttt                                              20

<210> SEQ ID NO 58
<211> LENGTH: 21
<212> TYPE: DNA
<213> ORGANISM: Artificial Sequence
<220> FEATURE:
<223> OTHER INFORMATION: Artificial Probe

<400> SEQUENCE: 58
ttggaaagtg agtattccat g                                            21

<210> SEQ ID NO 59
<211> LENGTH: 21
<212> TYPE: DNA
<213> ORGANISM: Artificial Sequence
<220> FEATURE:
<223> OTHER INFORMATION: Artificial Probe

<400> SEQUENCE: 59
ttggaaagtg aatattccat g                                            21
```

```
<210> SEQ ID NO 60
<211> LENGTH: 21
<212> TYPE: DNA
<213> ORGANISM: Artificial Sequence
<220> FEATURE:
<223> OTHER INFORMATION: Artificial Probe

<400> SEQUENCE: 60
acttcatcca gatatgtaaa a                                              21

<210> SEQ ID NO 61
<211> LENGTH: 21
<212> TYPE: DNA
<213> ORGANISM: Artificial Sequence
<220> FEATURE:
<223> OTHER INFORMATION: Artificial Probe

<400> SEQUENCE: 61
acttcatcca ggtatgtaaa a                                              21

<210> SEQ ID NO 62
<211> LENGTH: 21
<212> TYPE: DNA
<213> ORGANISM: Artificial Sequence
<220> FEATURE:
<223> OTHER INFORMATION: Artificial Probe

<400> SEQUENCE: 62
tatagttctt ggagaaggtg g                                              21

<210> SEQ ID NO 63
<211> LENGTH: 21
<212> TYPE: DNA
<213> ORGANISM: Artificial Sequence
<220> FEATURE:
<223> OTHER INFORMATION: Artificial Probe

<400> SEQUENCE: 63
tatagttctt tgagaaggtg g                                              21

<210> SEQ ID NO 64
<211> LENGTH: 21
<212> TYPE: DNA
<213> ORGANISM: Artificial Sequence
<220> FEATURE:
<223> OTHER INFORMATION: Artificial Probe

<400> SEQUENCE: 64
tctttagcaa ggtgaataac t                                              21

<210> SEQ ID NO 65
<211> LENGTH: 21
<212> TYPE: DNA
<213> ORGANISM: Artificial Sequence
<220> FEATURE:
<223> OTHER INFORMATION: Artificial Probe

<400> SEQUENCE: 65
tctttagcaa cgtgaataac t                                              21

<210> SEQ ID NO 66
<211> LENGTH: 21
<212> TYPE: DNA
<213> ORGANISM: Artificial Sequence
<220> FEATURE:
<223> OTHER INFORMATION: Artificial Probe
```

```
<400> SEQUENCE: 66
gagtggaggt caacgagcaa g                                      21

<210> SEQ ID NO 67
<211> LENGTH: 21
<212> TYPE: DNA
<213> ORGANISM: Artificial Sequence
<220> FEATURE:
<223> OTHER INFORMATION: Artificial Probe

<400> SEQUENCE: 67
gagtggagat caacgagcaa g                                      21

<210> SEQ ID NO 68
<211> LENGTH: 20
<212> TYPE: DNA
<213> ORGANISM: Artificial Sequence
<220> FEATURE:
<223> OTHER INFORMATION: Artificial Probe

<400> SEQUENCE: 68
gtggaggtca atgagcaaga                                        20

<210> SEQ ID NO 69
<211> LENGTH: 21
<212> TYPE: DNA
<213> ORGANISM: Artificial Sequence
<220> FEATURE:
<223> OTHER INFORMATION: Artificial Probe

<400> SEQUENCE: 69
tggtaatagg acatctccaa g                                      21

<210> SEQ ID NO 70
<211> LENGTH: 21
<212> TYPE: DNA
<213> ORGANISM: Artificial Sequence
<220> FEATURE:
<223> OTHER INFORMATION: Artificial Probe

<400> SEQUENCE: 70
tggtaataag acatctccaa g                                      21

<210> SEQ ID NO 71
<211> LENGTH: 21
<212> TYPE: DNA
<213> ORGANISM: Artificial Sequence
<220> FEATURE:
<223> OTHER INFORMATION: Artificial Probe

<400> SEQUENCE: 71
actccagcat agatgtggat a                                      21

<210> SEQ ID NO 72
<211> LENGTH: 21
<212> TYPE: DNA
<213> ORGANISM: Artificial Sequence
<220> FEATURE:
<223> OTHER INFORMATION: Artificial Probe

<400> SEQUENCE: 72
actccagcat acatgtggat a                                      21
```

```
<210> SEQ ID NO 73
<211> LENGTH: 21
<212> TYPE: DNA
<213> ORGANISM: Artificial Sequence
<220> FEATURE:
<223> OTHER INFORMATION: Artificial Probe

<400> SEQUENCE: 73
gaactgtgag ccgagtcttt a                                              21

<210> SEQ ID NO 74
<211> LENGTH: 21
<212> TYPE: DNA
<213> ORGANISM: Artificial Sequence
<220> FEATURE:
<223> OTHER INFORMATION: Artificial Probe

<400> SEQUENCE: 74
gaactgtgag ctgagtcttt a                                              21

<210> SEQ ID NO 75
<211> LENGTH: 21
<212> TYPE: DNA
<213> ORGANISM: Artificial Sequence
<220> FEATURE:
<223> OTHER INFORMATION: Artificial Probe

<400> SEQUENCE: 75
tggttgactt ggtaggttta c                                              21

<210> SEQ ID NO 76
<211> LENGTH: 20
<212> TYPE: DNA
<213> ORGANISM: Artificial Sequence
<220> FEATURE:
<223> OTHER INFORMATION: Artificial Probe

<400> SEQUENCE: 76
tggttgactt gtaggtttac                                                20

<210> SEQ ID NO 77
<211> LENGTH: 21
<212> TYPE: DNA
<213> ORGANISM: Artificial Sequence
<220> FEATURE:
<223> OTHER INFORMATION: Artificial Probe

<400> SEQUENCE: 77
ttaaaatggt gagtaagaca c                                              21

<210> SEQ ID NO 78
<211> LENGTH: 21
<212> TYPE: DNA
<213> ORGANISM: Artificial Sequence
<220> FEATURE:
<223> OTHER INFORMATION: Artificial Probe

<400> SEQUENCE: 78
ttaaaatggc gagtaagaca c                                              21

<210> SEQ ID NO 79
<211> LENGTH: 21
<212> TYPE: DNA
<213> ORGANISM: Artificial Sequence
<220> FEATURE:
<223> OTHER INFORMATION: Artificial Probe
```

```
<400> SEQUENCE: 79
tgcaacagtg gaggaaagcc t                                              21

<210> SEQ ID NO 80
<211> LENGTH: 21
<212> TYPE: DNA
<213> ORGANISM: Artificial Sequence
<220> FEATURE:
<223> OTHER INFORMATION: Artificial Probe

<400> SEQUENCE: 80
tgcaacagtg aaggaaagcc t                                              21

<210> SEQ ID NO 81
<211> LENGTH: 21
<212> TYPE: DNA
<213> ORGANISM: Artificial Sequence
<220> FEATURE:
<223> OTHER INFORMATION: Artificial Probe

<400> SEQUENCE: 81
atttagaaaa aacttggatc c                                              21

<210> SEQ ID NO 82
<211> LENGTH: 21
<212> TYPE: DNA
<213> ORGANISM: Artificial Sequence
<220> FEATURE:
<223> OTHER INFORMATION: Artificial Probe

<400> SEQUENCE: 82
atttagaaaa aagttggatc c                                              21

<210> SEQ ID NO 83
<211> LENGTH: 16
<212> TYPE: DNA
<213> ORGANISM: Artificial Sequence
<220> FEATURE:
<223> OTHER INFORMATION: Artificial Probe

<400> SEQUENCE: 83
aggactccat gcccag                                                    16
```

DIFFERENTIATING HOMOZYGOUS, HETEROZYGOUS AND WILD-TYPE ALLELES USING A MULTIPLEXED HYBRIDIZATION-MEDIATED ASSAY

RELATED APPLICATIONS

This application is a continuation of application U.S. Ser. No. 10/847,046, filed May 17, 2004, which claims priority to U.S. Provisional Application No. 60/470,806, filed May 15, 2003, priority to both of which is hereby claimed.

BACKGROUND

The standard method of genomic analysis for mutations and polymorphisms, including for CF, is the "dot-blot" method. Samples including target strands are spotted onto a nitrocellulose, support, and then contacted with labeled probes complementary to the mutations or polymorphic regions. The labels allow detection of probe hybridization to immobilized complementary target sequences, as unbound labeled probes are removed by washing. In another method—a "reverse dot-blot format"—an array of oligonucleotide probes is bound to a solid support, and then contacted with a sample including target sequences of interest. See, e.g., U.S. Pat. No. 5,837,832.

Both methods of assaying mutations or polymorphisms have significant disadvantages. The dot-blot method is itself labor-intensive. It can also yield erroneous results due to the inaccurate reading of assay signals, usually done by autoradiography, which adds further labor, as the probes must be frequently re-labeled. The method described in U.S. Pat. No. 5,837,832 involves a complex and costly on chip synthesis of an array of oligonucleotides, an approach which is better-suited for large-scale genomic analysis and is neither practical nor cost-effective for diagnostic applications requiring only a limited but changing number of probes.

An assay method suitable for multiplexed analysis which avoids many of the problems associated with the above methods involves use of random encoded arrays of microparticles, where the encoding indicates the identity of an oligonucleotide probe molecule bound thereto. See U.S. patent application Ser. No. 10/204,799: "Multianalyte Molecular Analysis Using Application-Specific Random Particle Arrays." The bead array is contacted with labeled amplicons, generated from a patient sample, and the labels are then detected (if the labels are fluorescent, the detection can be with optical means) and the bound amplicons are identified by decoding of the array.

In a multiplexed hybridization assay, cross-hybridization among mismatched, but closely homologous, probes and amplicons can generate false positive signals. Thus, the assay should be designed to minimize such effects. A number of mutations and polymorphisms are significant only if they are homozygous, and therefore, to be useful in such cases, the assay must be capable of discriminating heterozygotes from homozygotes. Also, in determining the assay results, where both the encoding method for the beads and the determination of assay results is with optically detectable means, the encoding on the beads can cause spectral leakage, which can be affect the assay signal discrimination. A method of correcting for such spectral leakage is also needed.

Cystic fibrosis ("CF") is one of the most common recessive disorders in Caucasians, with an occurrence of 1 in 2000 live births in the United States. Mutations in the cystic fibrosis (CF) transmembrane conductance regulator (CFTR) gene are associated with the disease. The number of CFTR mutations is growing continuously and rapidly, and more than 1,000 mutations have been detected to date. See Kulczycki L. L., et al. (2003), Am J Med Genet 116:262-67. Population studies have indicated that the most common CF mutation, a deletion of the 3 nucleotides that encode phenylalanine at position 508 of the CFTR amino acid sequence (designated $\Delta$F508), is associated with approximately 70% of the cases of cystic fibrosis. This mutation results in the failure of an epithelial cell chloride channel to respond to cAMP (Frizzell R. A. et al. (1986) Science 233:558-560; Welsh, M. J. (1986) Science 232:1648-1650.; Li, M. et al. (1988) Nature 331:358-360; Quinton, P. M. (1989) Clin. Chem. 35:726-730). In airway cells, this leads to an imbalance in ion and fluid transport. It is widely believed that this causes abnormal mucus secretion observed in CF patients, and ultimately results in pulmonary infection and epithelial cell damage. A number of mutations are associated with CF, and researchers continue to reveal new mutations associated with the disease. The American College of Medical Genetics ("ACMG") has recommended a panel of 25 of the most common CF-associated mutations in the general population, especially those in Ashkenazi Jewish and African-American populations. A multiplexed hybridization assay for CF-associated mutations in the general population would test for this panel.

SUMMARY

Described are practical and cost-effective methods of assay design and assay image correction, useful for multiplexed genetic screening for mutations and polymorphisms, including CF-related mutants and polymorphs, using an array of probe pairs (in one aspect, where one member is complementary to a particular mutant or polymorphic allele and the other member is complementary to a corresponding wild type allele), with probes bound to encoded particles (e.g., beads) wherein the encoding allows identification of the attached probe. The design methods disclosed herein were used to design an assay for CF-related mutations by hybridization-mediated multiplexed analysis, and were extensively validated in many patient samples, and demonstrated to be capable of identifying the most common mutations, including mutations in exons 3, 4, 5, 7, 9, 10, 11, 13, 14b, 16, 18, 19, 20, 21 and introns 8, 12, 19 of the CFTR gene.

Before hybridization, the region of interest in the genomic sample is amplified with two primers, one for each strand in the region of interest. Of the two strands generated in the PCR amplification step, one is arbitrarily designated herein as "sense" and one as "anti-sense." In certain instances, it is desirable to select, for subsequent mutation analysis by hybridization, either the sense target strand (to be hybridized to sense probes) or the anti-sense target strand—to be hybridized to anti-sense probes. Strand selection is accomplished, for example, by post-PCR digestion of a phosphorylated strand. In particular, strand switching is desirable whenever probe-target combinations (e.g., sense-probe/sense target hybridization) involving a stable mismatch configuration, such as a G-T base pairing, can be avoided.

Also disclosed are methods of selecting probes and amplicons for genetic screening for mutations and polymorphisms. The method of selecting probes and amplicons involves the following steps:

providing a family of single-stranded MP amplicons in which one strand is designated sense and the complementary strand is designated anti-sense, said MP amplicons including amplified segments of the genome on which said genetic mutations or polymorphisms are located;

selecting complementary MP probes for each member of said family of MP amplicons;

examining the degree of homology between either the complementary MP probes or between the family of MP amplicons;

dividing said MP probes into one or more probe sets, and dividing said MP amplicons into sets such that the members of each amplicon set are complementary to the members of one probe set, said division based on avoiding homology greater than an acceptance level between probes in the same set or between MP amplicons in the same set;

performing for each said set of amplicons in turn, the following steps for each MP amplicon in said set, in succession:

(a)(i) determining whether, upon contacting a sense MP amplicon with a probe set which includes a complementary MP probe to said sense amplicon, the degree of cross-hybridization of said sense MP amplicon with other MP probes in the probe set will exceed an acceptance level; and, if not:

(a)(ii) retaining said sense MP amplicon in the amplicon set and the complementary MP probe in the probe set, and repeating step (a)(i) for another MP amplicon in said family;

(b)(i) but if said degree of cross-hybridization does exceed said acceptance level: replacing, in the probe set, the cross-hybridizing MP probe with the complementary anti-sense MP probe, and replacing, in the amplicon set, the complementary sense MP amplicon with the anti-sense MP amplicon complementary to said anti-sense MP probe, and (b)(ii) repeating step (a)(i) and if the degree of cross-hybridization is within the acceptance level: retaining said anti-sense MP probe and corresponding complementary anti-sense MP amplicon in their respective sets and repeating step (a)(i);

(b)(iii) but if the degree of cross-hybridization exceeds the acceptance level after repeating step (a)(i): determining whether, upon contacting said anti-sense MP amplicon with the MP probes in any other set, the degree of cross-hybridization is within the acceptance level, and if so, placing the anti-sense MP probe complementary to said anti-sense MP amplicon into said set and placing said anti-sense MP amplicon into the set of complementary anti-sense MP amplicons; but if the degree of cross-hybridization exceeds the acceptance level following such determination for each existing probe set, reverting to the original sense MP probe and complementary sense MP amplicon and placing said sense MP probe and said complementary sense MP amplicon each into a new set, and (c) repeating steps (a) to (c) for another sense MP amplicon in said family.

Also disclosed is a method for design of pairs of probes (with a member respectively complementary to a mutant and a wild type amplicon) for hybridization to labeled amplicons generated by amplification of samples and wild type controls. For each anticipated variant, probes are provided in pairs, with one member complementary to the wild type sequence and the other to the variant sequence, the two sequences often differing by only one nucleotide. One method to enhance the reliability of hybridization-mediated multiplexed analysis of polymorphisms (hMAP) is to determine the ratio of the signals generated by the capture of the target matched and mismatched probes and to set relative ranges of values indicative of normal and heterozygous or homozygous variants.

The method set forth above for selecting probes and amplicons for genetic screening for mutations and polymorphisms, can be included as part of a method to select probe pairs (wild-type and variant), by including the following steps in the afore-described method:

providing a family of single-stranded WT amplicons in which one strand is designated sense and the complementary strand is designated anti-sense, said family representing respective amplified segments of a wild type genome which corresponds to each of the amplified segments of the genome which was amplified when producing the family of MP amplicons;

providing and selecting a sense or anti-sense WT probe so as to have both a sense WT probe and a corresponding sense MP probe in the same probe set or, or an anti-sense WT probe and a corresponding anti-sense MP probe in the same probe set;

determining: (i) whether the degree of cross-hybridization between a MP amplicon and a corresponding WT probe in a probe set, and between a WT amplicon and a corresponding MP probe in a probe set, will exceed the acceptance level and, if so, (ii) determining whether said degree of cross-hybridization will fall within the acceptance level if the selected sense or anti-sense MP and WT probes are replaced with the complementary WT and MP probes; and if so, (iii) determining whether said complementary WT and MP probes will exceed the acceptance level for cross-hybridization with amplicons complementary to other members of the same probe set, and if so, (iv) determining whether placing the complementary WT and MP probes into another probe set will exceed the acceptance level for cross-hybridization with amplicons complementary to other members of the same probe set, and if not: retaining the complementary WT and MP probes in said probe set; but if so, (v) repeating step (iv) for each existing probe set, and if said acceptance level is exceeded for each existing probe set, placing the complementary WT and MP probes into a new set and placing the complementary WT and MP amplicons into a corresponding new set.

Cross-hybridization is a concern in any assay involving multiplexed hybridization, and methods to avoid its deleterious effects on assay results are included herein. One method to correct for cross-hybridization in an array format, is to set a series of temperature increments, selected such that at each temperature, probe-target complexes containing particular mismatch configurations will denature, while those containing matched ("complementary") base pair configurations will remain intact. The signals generated by captured labeled strands hybridized to probes in the array are then monitored and recorded at each temperature set point. Analysis of the evolution of differential signals as a function of temperature allows correction for each mismatch expected to become unstable above a certain "melting" temperature. After all set points for all mismatches are determined, data gathered at lower temperatures can be corrected for all mismatches.

In another aspect, because the assay method herein relies on encoded beads to identify the probe(s) attached thereto, and the encoding in one embodiment is by way of dye staining, the assay signals are often produced by using fluorescent labels and removing background contributions. Specifically, a method of correcting the assay image is disclosed. That is, within the spectral band selected for the recording of the assay image, the recorded set of optical signatures produced by target capture to bead-displayed probes in the course of the assay are corrected for the effects of "spectral leakage" (a source of spurious contributions to the assay image from the residual transmission) of intensity emitted by bead-encoding dyes of lower wavelength. An assay design is provided herein in which a negative control bead is included in the random encoded array for each type of encoded bead that produces unacceptably large spectral leakage, for example, for beads containing different amounts of specific encoding dyes.

In the examples described herein, negative control beads display an 18-mer C polynucleotide in order to serve a secondary purpose, i.e., to permit correction of assay images for the effects of non-specific adsorption. Preferably, the background correction is performed by constructing a background map based on the random locations of each type of negative control bead, where each such type of negative control bead is included in the array at a pre-selected abundance. For each type of negative control bead within the array, a background map is generated by locating the centroids of the beads of that type, constructing the associated Voronoi tessellation by standard methods (as illustrated in FIG. 3; see, e.g., Seul, O'Gorman & Sammon, "Practical Algorithms for Image Analysis," Cambridge University Press, 2000; at page 222; incorporated by reference) and then filling each polygon which includes a bead with the intensity of such bead to produce a map (see, e.g., the map shown in FIG. 3). Optionally, standard filtering operations may be applied to smooth the map; that is, to average out effects from neighboring pixels. See, e.g., Seul, O'Gorman & Sammon, "Practical Algorithms for Image Analysis," Cambridge University Press, 2000 for description of a filter).

Such a map represents a finite sample of the entire background contributions to the assay image in a manner that accounts for certain non-linear optical effects associated with arrays composed of refractive beads, which effects are especially pronounced when the beads are placed into mechanical traps on a substrate surface. In addition, background maps will indicate non-uniformities in the background which may arise, for example, from non-uniform illumination or non-uniform distribution of target or analyte placed in contact with the bead array. Maps for negative control beads of different types, i.e., containing different amounts of encoding dyes and producing different degrees of spectral leakage, may be normalized to the same mean intensity and superimposed to increase the sampling rate.

The assay image may be corrected as follows by employing the background map. In certain instances, the map is simply subtracted from the assay image to produce a corrected assay image. In other embodiments, the background can be combined with a "flat fielding" step (See, e.g., Seul, O'Gorman & Sammon, "Practical Algorithms for Image Analysis," Cambridge University Press, 2000). In this procedure, the constant (i.e., the spatially non-varying) portions of the background map and assay image are subtracted, and the corrected assay image is divided by the corrected background map to obtain a "flat fielded" intensity map.

BRIEF DESCRIPTION OF THE FIGURES

FIG. 1 shows the results of hybridization of 29 different CFTR mutations; where the smaller open bars represent mutant hybridization, and where hybridization to the "normal" is represented by the larger black bars (e.g., EX-10 has a high degree of mutant hybridization).

FIG. 2 shows the results of hybridization of 29 CFTR mutations, with the mutations being different from those shown in FIG. 1.

DETAILED DESCRIPTION

Figure 3:
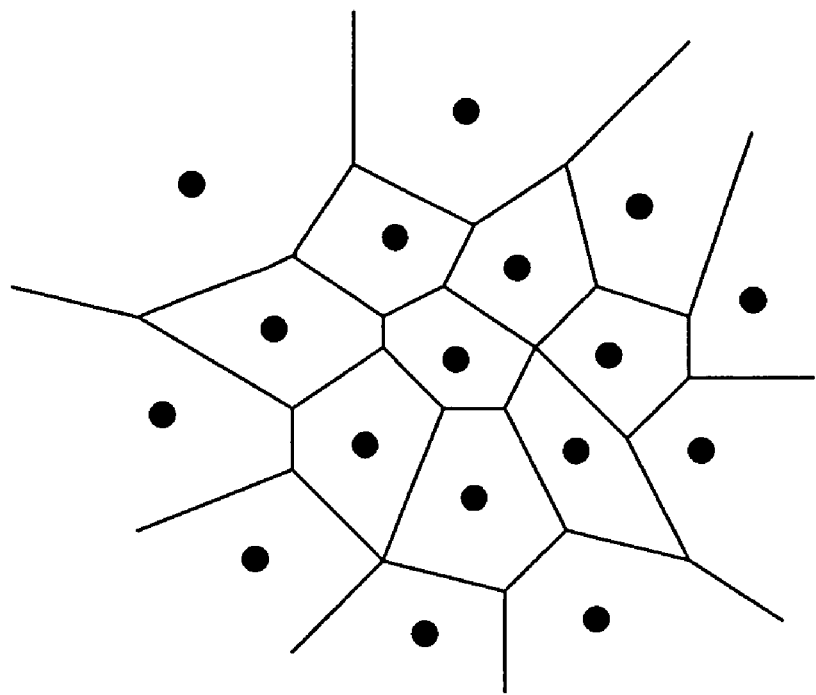
FIG. 3 shows a background map of negative control carriers for correcting array images.

Provided herein are methods for hybridization-mediated multiplexed analysis of polymorphisms (hMAP) of a designated set of designated mutations in he Cystic Fibrosis Transmembrane Conductance Regulator (CFTR) gene.

Probes used in the detection of mutations in a target sequence hybridize with high affinity to amplicons generated from designated target sites, when the entire amplicon, or a subsequence thereof, is fully complementary ("matched") to that of the probe, but hybridize with a lower affinity to amplicons which have no fully complementary portions ("mismatched"). Generally, the probes of the invention should be sufficiently long to avoid annealing to unrelated DNA target sequences. In certain embodiments, the length of the probe may be about 10 to 50 bases, or preferably about 15 to 25 bases, and more preferably 18 to 20 bases.

Probes are attached, via their respective 5' termini, using linker moieties through methods well known in the art, to encoded microparticles ("beads") having a chemically or physically distinguishable characteristic uniquely identifying the attached probe. Probes are designed to capture target sequences of interest contained in a solution contacting the beads. Hybridization of target to the probe displayed on a particular bead produces an optically detectable signature. The optical signature of each participating bead uniquely corresponds to the probe displayed on that bead. Prior to, or subsequent to the hybridization step, one may determine the identity of the probes by way of particle identification and detection, e.g., by decoding or using multicolor fluorescence microscopy.

The composition of the beads includes, but is not limited to, plastics, ceramics, glass, polystyrene, methylstyrene, acrylic polymers, paramagnetic materials, thoria sol, carbon graphite, titanium dioxide, latex or cross-linked dextrans such as sepharose, cellulose, nylon, cross-linked micelles and Teflon. See "Microsphere Detection Guide" from Bangs Laboratories, Fishers Ind. The particles need not be spherical and may be porous. The bead sizes may range from nanometers (e.g., 100 nm) to millimeters (e.g., 1 mm), with beads from about 0.2 micron to about 200 microns being preferred, more preferably from about 0.5 to about 5 micron being particularly preferred.

In certain embodiments, beads may be arranged in a planar array on a substrate prior to the hybridization step. Beads also may be assembled on a planar substrate to facilitate imaging subsequent to the hybridization step. The process and system described herein provide a high throughput assay format permitting the instant imaging of an entire array of beads and the simultaneous genetic analysis of multiple patient samples.

The array of beads may be a randomly encoded array, that is, the code associated with each bead, placed during assembly into a position within the array that is not known a priori, indicates the identity of oligonucleotide probes attached to said beads. Random encoded arrays may be formed according to the methods and processes disclosed in International Application No. PCT/US01/20179, incorporated herein by reference.

The bead array may be prepared by employing separate batch processes to produce application-specific substrates (e.g., chip at the wafer scale) to produce beads that are chemically encoded and attached to oligonucleotide probes (e.g., at the scale of about $10^8$ beads/100 µl suspension). These beads are combined with a substrate (e.g., silicon chip) and assembled to form dense arrays on a designated area on the substrate. In certain embodiments, the bead array contains 4000 of 3.2 µm beads has a dimension of 300 µm by 300 µm. With different size beads, the density will vary. Multiple bead arrays can also be formed simultaneously in discrete fluid compartments maintained on the same chip. Such methods are disclosed in U.S. application Ser. No. 10/192,352, entitled: "Arrays of Microparticles and Methods of Preparation Thereof," which is incorporated herein by reference. Bead arrays may be formed by the methods collectively referred to as "LEAPS™", as described in U.S. Pat. Nos. 6,251,691, 6,514,771; 6,468,811 all of which are also incorporated herein by reference.

Substrates (e.g., chips) used in the present invention may be a planar electrode patterned in accordance with the interfacial patterning methods of LEAPS by, e.g., patterned growth of oxide or other dielectric materials to create a desired configuration of impedance gradients in the presence of an applied AC electric field. Patterns may be designed so as to produce a desired configuration of AC field-induced fluid flow and corresponding particle transport. Substrates may be patterned on a wafer scale by invoking semiconductor processing technology. In addition, substrates may be compartmentalized by depositing a thin film of a UV-patternable, optically transparent polymer to affix to the substrate a desired layout of fluidic conduits and compartments to confine fluid in one or several discrete compartments, thereby accommodating multiple samples on a given substrate.

The bead arrays may be prepared by providing a first planar electrode that is in substantially parallel to a second planar electrode ("sandwich" configuration) with the two electrodes being separated by a gap and containing a polarizable liquid medium, such as an electrolyte solution. The surface or the interior of the second planar electrode is patterned with the interfacial patterning method. The beads are introduced into the gap. When an AC voltage is applied to the gap, the beads form a random encoded array on the second electrode (e.g., "chip"). And, also using LEAPS, an array of beads may be formed on a light-sensitive electrode ("chip"). Preferably, the sandwich configuration described above is also used with a planar light sensitive electrode and another planar electrode. Once again, the two electrodes are separated by a gap and contain an electrolyte solution. The functionalized and encoded beads are introduced into the gap. Upon application of an AC voltage in combination with a light, the beads form an array on the light-sensitive electrode.

In certain embodiments, beads may be associated with a chemically or optically distinguishable characteristic. This may be provided, for example, by staining beads with sets of optically distinguishable tags, such as those containing one or more fluorophore or chromophore dyes spectrally distinguishable by excitation wavelength, emission wavelength, excited-state lifetime or emission intensity. The optically distinguishable tags made be used to stain beads in specified ratios, as disclosed, for example, in Fulwyler, U.S. Pat. No. 4,717,655 (Jan. 5, 1988). Staining may also be accomplished by swelling of particles in accordance with methods known to those skilled in the art, (Molday, Dreyer, Rembaum & Yen, J. Mol Biol 64, 75-88 (1975); L. Bangs, "Uniform latex Particles, Seragen Diagnostics, 1984). For example, up to twelve types of beads were encoded by swelling and bulk staining with two colors, each individually in four intensity levels, and mixed in four nominal molar ratios. Alternatively, the methods of combinatorial color encoding described in International Application No. PCT/US 98/10719, incorporated herein by reference, can be used to endow the bead arrays with optically distinguishable tags. In addition to chemical encoding, beads may also be rendered magnetic by the processes described in International Application No. WO 01/098765.

In addition to chemical encoding of the dyes, the beads having certain oligonucleotide primers may be spatially separated ("spatial encoding"), such that the location of the beads provide certain information as to the identity of the beads placed therein. Spatial encoding, for example, can be accomplished within a single fluid phase in the course of array assembly by invoking LEAPS to assemble planar bead arrays in any desired configuration in response to alternating electric fields and/or in accordance with patterns of light projected onto the substrate.

LEAPS creates lateral gradients in the impedance of the interface between silicon chip and solution to modulate the electrohydrodynamic forces that mediate array assembly. Electrical requirements are modest: low AC voltages of typically less than $10V_{pp}$ are applied across a fluid gap of typically 100 µm between two planar electrodes. This assembly process is rapid and it is optically programmable: arrays containing thousands of beads are formed within seconds under electric field. The formation of multiple subarrays, can also occur in multiple fluid phases maintained on a compartmentalized chip surface.

Subsequent to the formation of an array, the array may be immobilized. For example, the bead arrays may be immobilized, for example, by application of a DC voltage to produce random encoded arrays. The DC voltage, set to typically 5-7 V (for beads in the range of 2-6 µm and for a gap size of 100-150 µm) and applied for <30 s in "reverse bias" configuration so that an n-doped silicon substrate would form the anode, causes the array to be compressed to an extent facilitating contact between adjacent beads within the array and simultaneously causes beads to be moved toward the region of high electric field in immediate proximity of the electrode surface. Once in sufficiently close proximity, beads are anchored by van der Waals forces mediating physical adsorption. This adsorption process is facilitated by providing on the bead surface a population of "tethers" extending from the bead surface; polylysine and streptavidin have been used for this purpose.

In certain embodiments, the particle arrays may be immobilized by chemical means, e.g, by forming a composite gel-particle film. In one exemplary method for forming such gel-composite particle films, a suspension of microparticles is provided which also contain all ingredients for subsequent in-situ gel formation, namely monomer, crosslinker and initiator. The particles are assembled into a planar assembly on a substrate by application of LEAPS, e.g., AC voltages of 1-20 $V_{p-p}$ in a frequency range from 100's of hertz to several kilohertz are applied between the electrodes across the fluid gap. Following array assembly, and in the presence of the applied AC voltage, polymerization of the fluid phase is triggered by thermally heating the cell ~40-45° C. using an infra-red (IR) lamp or photometrically using a mercury lamp source, to effectively entrap the particle array within a gel. Gels may be composed of a mixture of acrylamide and bisacrylamide of varying monomer concentrations from 20% to 5% (acrylamide:bisacrylamide=37.5:1, molar ratio), or any other low viscosity water soluble monomer or monomer mixture may be used as well. Chemically immobilized functionalized microparticle arrays prepared by this process may be used for a variety of bioassays, e.g., ligand receptor binding assays.

In one example, thermal hydrogels are formed using azodiisobutyramidine dihydrochloride as a thermal initiator at a low concentration ensuring that the overall ionic strength of the polymerization mixture falls in the range of ~0.1 mM to 1.0 mM. The initiator used for the UV polymerization is Irgacure 2959® (2-Hydroxy-4'-hydroxyethoxy-2-methyl-propiophenone, Ciba Geigy, Tarrytown, N.Y.). The initiator is added to the monomer to give a 1.5% by weight solution.

In certain embodiments, the particle arrays may be immobilized by mechanical means. For example, an array of microwells may be produced by standard semiconductor processing methods in the low impedance regions of the silicon substrate. The particle arrays may be formed using such structures by, e.g., utilizing LEAPS mediated hydrodynamic and ponderomotive forces are utilized to transport and accumulate particles on the hole arrays. The AC field is then switched off and particles are trapped into microwells and thus mechanically confined. Excess beads are removed leaving behind a geometrically ordered random bead array on the substrate surface.

Substrates (e.g., chips) can be placed in one or more enclosed compartment, permitting interconnection. Reactions can also be performed in an open compartment format similar to microtiter plates. Reagents may be pipetted on top of the chip by robotic liquid handling equipment, and multiple samples may be processed simultaneously. Such a format accommodates standard sample processing and liquid handling for existing microtiter plate format and integrates sample processing and array detection.

Encoded beads can also be assembled, but not in an array, on the substrate surface. For example, by spotting bead suspensions into multiple regions of the substrate and allowing beads to settle under gravity, assemblies of beads can be formed on the substrate. In contrast to the bead arrays formed by LEAPS, these assemblies generally assume disordered configurations of low-density or non-planar configurations involving stacking or clumping of beads thereby preventing imaging of affected beads. However, the combination of spatial and color encoding attained by spotting mixtures of chemically encoded beads into a multiplicity of discrete positions on the substrate still allows multiplexing.

In certain embodiments, a comparison of an assay with a decoded image of the array can be used to reveal chemically or physically distinguishable characteristics, and the elongation of probes. This comparison can be achieved by using, for example, an optical microscope with an imaging detector and computerized image capture and analysis equipment. The assay image of the array is taken to detect the optical signature that indicates the probe elongation. The decoded image may be taken to determine the chemically and/or physically distinguishable characteristics that uniquely identify the probe displayed on the bead surface. In this way, the identity of the probe on each particle in the array may be identified by a distinguishable characteristic.

Image analysis algorithms may be used in analyzing the data obtained from the decoding and the assay images. These algorithms may be used to obtain quantitative data for each bead within an array. The analysis software automatically locates bead centers using a bright-field image of the array as a template, groups beads according to type, assigns quantitative intensities to individual beads, rejects "blemishes" such as those produced by "matrix" materials of irregular shape in serum samples, analyzes background intensity statistics and evaluates the background-corrected mean intensities for all bead types along with the corresponding variances. Examples of such algorithms are set forth in International Application No. WO 01/098765.

The probe hybridization may be indicated by a change in the optical signature, e.g., of the beads associated with the probes. This can be done using labeling methods well known in the art, including direct and indirect labeling. In certain embodiments, fluorophore or chromophore dyes may be attached to one of the nucleotides added during the probe hybridization, such that the probe hybridization to its target changes the optical signature of beads (e.g., the fluorescent intensities change, thus providing changes in the optical signatures of the beads).

Described herein are methods and compositions to conduct accurate polymorphism analysis for highly polymorphic target regions. Analogous considerations pertain to designs, compositions and methods of multiplexing PCR reactions.

The density of polymorphic sites in highly polymorphic loci makes it likely that designated probes directed to selected polymorphic sites, when annealing to the target subsequence proximal to the designated polymorphic site, will overlap adjacent polymorphic sites. That is, an oligonucleotide probe, designed to interrogate the configuration of the target at one of the selected polymorphic sites, and constructed with sufficient length to ensure specificity and thermal stability in annealing to the correct target subsequence, will align with other nearby polymorphic sites. These interfering polymorphic sites may include the non-designated selected sites as well as non-selected sites in the target sequence.

The design of covering probe sets is described herein in connection with hybridization-mediated multiplexed analysis of polymorphisms in the scoring of multiple uncorrelated designated polymorphisms, as in the case of mutation analysis for CF carrier screening. In this instance, the covering set for the entire multiplicity of mutations contains multiple subsets, each subset being associated with one designated site. In the second instance, the covering set contains subsets constructed to minimize the number of probes in the set, as elaborated herein.

Arrays of bead-associated probes can be used in the hybridization-mediated analysis of a set of mutations within the context of a large set of non-designated mutations and polymorphisms in the Cystic Fibrosis Transmembrane Conductance Regulator (CFTR) gene. Each of the designated mutations in the set is associated with the disease and must be independently scored. In the case of a point mutation, two encoded probes are provided to ensure alignment with the designated site, one probe complementary to the wild-type, the other to the mutated or polymorphic target sequence.

In certain embodiments, the identification of the specific target configuration encountered in the non-designated sites is of no interest so long as one of the sequences provided in the covering probe set matches the target sequence sufficiently closely—and thus matches the target sequence exactly to ensure hybridization. In such a case, all or some of the covering probes may be assigned the same code; in a preferred embodiment, such probes may be associated with the same solid support ("probe pooling"). Probe pooling reduces the number of distinguishable solid supports required to represent the requisite number of probes. In one particularly preferred embodiment, solid supports are provided in the form of a set or array of distinguishable microparticles which may be decoded in situ. Inclusion of additional probes in the covering set to permit identification of additional polymorphisms in the target region is a useful method to elucidate haplotypes for various populations.

Suitable probes may be designed to correspond to the known alleles within the CFTR gene locus. A number of polymorphisms and mutant alleles are known and available from literature and other sources.

Standard methods of temperature control are readily applied to set the operating temperature of, or to apply a preprogramed sequence of temperature changes to, single chips or to multichip carriers. When combined with the direct imaging of entire arrays of encoded beads as provided in the READ™ format of multiplexed analysis, the application of preprogrammed temperature cycles provides real-time on-chip amplification of elongation products. Given genomic, mitochondrial or other DNA, linear on-chip amplification eliminates the need for pre-assay DNA amplification such as PCR, thereby dramatically shortening the time required to complete the entire typing assay. Time-sensitive applications such as cadaver typing are thereby enabled. More importantly, this approach will eliminate the complexities of PCR multiplexing, a limiting step in many genetic screening and polymorphism analyses. In a preferred embodiment, a fluidic cartridge provides for sample and reagent injection, as well as temperature control.

The designs, compositions and methods described herein also pertain to the multiplexed amplification of nucleic acid samples. In a preferred embodiment, covering sets of PCR primers composed of priming and annealing subsequences are used for target amplification.

Described below is a series of steps for selecting an appropriate array of probes and targets for hybridization analysis.

Task:

Identify ("select") a set of probes, P, to perform one or more concurrent, "multiplexed" reactions permitting hybridization-mediated interrogation of nucleic acid sequences in order to determine the composition at each of a set of designated polymorphic sites, $S=\{S_1, Y, S_N\}$ said sites being located on M< or =N nucleic acid strands $T:=\{T_1, Y, T_M\}$ ("targets").

Targets—The collection, T, of targets, $\{T_i=(m_i, \sigma_i); 1< \text{or} =i< \text{or} =M\}$, is generated in a polymerase chain reaction (PCR) using PCR primers designed to place as many polymorphisms or mutations on each single target under the condition that the target length $l_i$ not exceed a preset maximal length, $l_{max}$, and wherein the i-th target, $T_i$ of length $l_i$ is further characterized by:

a multiplicity, $m_i$, giving the number of said designated polymorphisms (or mutations), wherein $\Sigma(i=1; i=M)$ $m_i=N$; and an orientation, $\sigma_i$, wherein $\sigma_i=+1$ for a sense ("cis") strand; or $\sigma_i=-1$ for an anti-sense ("trans") strand.

Probes—Mutation analysis preferably will involve the interrogation of each designated mutation site, $S_k$, by hybridization of the corresponding target to at least two designated interrogation probes, $P_k^N$ and $P_k^V$, of which at least a first probe, $P_k^N$, has a sequence that is complementary to the normal ("wild-type") composition, and of which at least a second probe, $P_k^V$, has a sequence that is complementary to a variant ("mutant") composition. In the presence of polymorphisms or mutations at sites within the interrogated subsequence other than the designated sites, it generally will be desirable to provide "degenerate" probes matching the anticipated compositions at non-designated sites. The designation $P_k=P_k(S_k)$ hereinafter is understood to refer to all probes directed to the k-th designated site such that $P_k$ is characterized by a number of probes, each of these probes having an orientation, $\sigma_{ik}$, opposite to that of the cognate target.

Specifically, probes are to be selected, and probe-target reactions are to be configured in a manner involving one or more sets of reactions, each of these reactions being performed in a separate container, in such a way as to minimize the interaction of any target subsequence containing a designated polymorphic site or mutation, $S_k$, with any but its corresponding designated probes, $P_k$.

Strategy—While not necessarily generating an optimal configuration, the following "heuristic" strategy provides the basis for a systematic process of assay optimization as a function of critical parameters including a maximal acceptable degree of similarity between two sequences, expressed in terms of a homology score, as well as a maximal acceptable level of "cross-hybridization", manifesting itself in magnitude of "off-diagonal" elements, $P_i$ $T_j$ of a co-affinity matrix (see U.S. application Ser. No. 10/204,799, entitled: "Multi-analyte molecular analysis using application-specific random particle arrays") showing the degree of interaction between all probes and all targets in a given group or set.

To minimize cross-hybridization between any given target and probes directed to other targets, distribute targets and their corresponding probes—into a number, C, of containers in order to perform C separate "multiplexed" hybridization reactions, said number being chosen to be as small as possible given a preset maximal acceptable level of sequence similarity ("maximal homology score") between targets in the same container.

To minimize cross-hybridization between any given target and probes directed to other targets in the same container, switch the orientation of such other targets and that of their corresponding probes, allowing for the possible reassignment of any target to another, possibly new container.

Certain targets may have more than one region, each having a designated probe in the array which hybridizes with it. To minimize cross-hybridization as well as competitive hybridization within the same container in such case, reduce the multiplicity of such an "offending" target by redesigning the PCR primer sets in order to produce two (or more) smaller targets to replace the original single target, each of the new targets having a lower multiplicity of hybridization regions than the original.

Implementation—The pseudocode below provides a description of the heuristic process of configuring the reaction so as to minimize cross-hybridization.

---

I - Assign targets - and cognate probes - to c sets ("Containers")

```
c = 0; DO
{
    REFSEQ = SelectTarget(T);          /* randomly pick a target
                                          sequence from given collection,
                                          T*/
    ShrinkCollection (T, 1);           /* remove selected
                                          target from collection */
    S = L(c);
    InitializeList (L(g), REFSEQ);     /* place selected target
                                          into    new    set
                                          ("group")implemented in the
                                          form of a list, S */
    AlignTargets (REFSEQ, T, HScores); /* align remaining targets to
                                          REFSEQ
                                          by pairwise alignment
                                          or multiple sequence
                                          alignment;    return
                                          homology scores */
    SortTargets (HScores, T);                /* rank target
                                          seq's in the order of increasing
                                          homology score with
                                          respect to REFSEQ;
                                          first entry least similar,
                                          last entry most similar
                                          to REFSEQ */
```

| I - Assign targets - and cognate probes - to c sets ("Containers") | |
|---|---|
| t = AssignTargets (maxHSCORE, S, , T); | /* remove targets from collection in the order of increasing homology scores up to maxHScore and place them into the list, starting at top; return number of targets assigned to the list, S */ |
| ShrinkCollection (T , t); | /* remove t selected targets from collection */ |
| c++;<br>}WHILE ( T not EMPTY); | |

Optionally, one or more lists may be pruned should they contain more than an acceptable number of targets (for example, if it is determined, based on too many targets in a list, that maxHScore should be lowered) by removing targets from the bottom of one or more of the lists and placing them back into the collection T.

| II - Refine group configuration | |
|---|---|
| FOR ( i=0; i<c; i++) | /*examine each group in turn */ |
| { | |
|    S = L(i); | /* List S holds targets in current group */ |
|    PofS = SelectProbes ( P, S); | /* select from P all probes directed to targets in current list */ |
| | /* each probe is designed to match at least one target - this is referred to as the probe cognate for that target; NOTE: refers to diagonal elements in co-affinity matrix */ |
|    WHILE (S not EMPTY)<br>   {<br>      T = PopTarget (S);<br>      PerformProbeTargetRxn (PofS, T); | /* place T in contact with all selected probes, preferably arranged in a probe array */ |
|       FOR (each probe, P, in PofS)<br>      {<br>         I = DetermineInteractionStrength (P, T); | |
| | /* eliminate unacceptably large off-diagonal element in co-affinity matrix*/ |
|          IF( (P not cognate to T) AND (I > maxI) )<br>         {<br>            FlipOrientation (P); | /* flip probe orientation */ |
|             FlipOrientation (TcP);<br>            /* flip orientation of target cognate to P */<br>         }<br>      } | |
| | /* check "flipped" targets in list S*/ |
|       flippedT = PopTarget (S);<br>      PerformProbeTargetRxn (PofS, flippedT); | /* place T in contact with all selected probes, preferably arranged in a probe array */ |
|       FOR (each probe, P, in PofS)<br>      {<br>         I = DetermineInteractionStrength (P, flippedT); | |

-continued

| II - Refine group configuration |
|---|

```
                                            /* eliminate
                                            unacceptably large off-
                                            diagonal element in co-
                                            affinity matrix*/
            IF( (P not cognate to flippedT) AND (I > maxI) )
            {
                    PushTarget (flippedT, TempList);    /* Place flipped
target
                                                        into    temporary
list */
            }
        }
    }
}
S = TempList;                           /* List S holds flipped targets in temp
list */
                                        /* Check targets in temp list */
WHILE (S not EMPTY)
{
    T = PopTarget (S);
    FOR (j=0; j <c; j++)
    {
            IF( L(j) != L(T) )          /* Check T against probes in all
existing lists
                                        with exception of those in T's original
list */
            {
                L = L(j);
                PofL = SelectProbesFrom List (L);       /* select probes in
    Group L */
                PerformProbeTargetRxn (PofL, T)         /* place T in contact
                                                        with all selected probes,
                                                        preferably arranged in a probe
                                                        array */
                FOR (each probe, P, in PofL)
                {
                    I = DetermineInteractionStrength (P, T);
                                                        /* eliminate unacceptably large
                                                        off-diagonal element in
                                                        co-affinity matrix*/
                    IF( (P not cognate to T) AND (I > maxI) )
                    {
                        FlipOrientation (T));           /* flip target orientation
                                                        back to original */
                        FlipOrientation (PcT); /* flip orientation of
                                                                        p
                                                                        r
                                                                        o
                                                                        b
                                                                        e
                                                        cognate to target T */
                        PushTarget(T, NewList);    /* init new group
*/
                    }
                }
            }
        }
    }
}
            FlipOrientation (P);                    /* flip probe orientation
                                                    */
            FlipOrientation (TcP);
            /* flip orientation of target cognate to P */
```

EXAMPLE I

CFTR Assay

Genomic DNA extracted from several patients was amplified with corresponding primers in a multiplex PCR (mPCR) reaction. The PCR conditions and reagent compositions were as follows:

PRIMER DESIGN: One of the primers (sense or antisense, depending on design considerations, discussed below) was modified with a label (such as, Cy3, Cy5 and Cy5.5) at the 5' end and the corresponding primer for the complementary sequence had a phosphate group added at the 5' end, so that the amplicon could be digested by λ exonuclease during post-PCR processing of the target (see below). Hybridization was detected by detection of the dyes (Cy3, Cy5 or Cy5.5) in the hybridized product. Multiplex PCR (mPCR) was performed in two groups with the following primers (Tables I and II), and with the reagents and under the conditions listed below. The exon number where the mutation is located appears below in the left-had column of Tables I and II.

TABLE I

Artificial sequence artificial primer
mPCR Group I Primers: ("Cy" denotes a dye label,
and "P" denotes a phosphate modification, at the
5' end of the primer)

| | | |
|---|---|---|
| EX-5-1-Cy | GTC AAG CCG TGT TCT A GAT | SEQ ID NO.:1 |
| EX-5-2-P | GTT GTA TAA TTT ATA ACA ATA GT | SEQ ID NO.:2 |
| EX-7-1-P | AC TTC AAT AGC TCA GCC TTC | SEQ ID NO.:3 |
| EX-7-2-Cy | TAT GGT ACA TTA CCT GTA TTT TG | SEQ ID NO.:4 |
| EX-9-1-P | TGG TGA CAG CCT CTT CTT | SEQ ID NO.:5 |
| EX-9-2-Cy | GAA CTA CCT TGC CTG CTC CA | SEQ ID NO.:6 |
| EX-12-1-P | TCT CCT TTT GGA TAC CTA GAT | SEQ ID NO.:7 |
| EX-12-2-Cy | TGA GCA TTA TAA GTA AGG TAT | SEQ ID NO.:8 |
| EX-13-1-P | AGG TAG CAG CTA TTT TTA TGG | SEQ ID NO.:9 |
| EX-13-2-Cy | ATC TGG TAC TAA GGA CAG | SEQ ID NO.:10 |
| EX-14B-1-P | TCT TTG GTT GTG CTG TGG CT | SEQ ID NO.:11 |
| EX-14B-2-Cy | ACA ATA CAT ACA AAC ATA GT | SEQ ID NO.:12 |
| EX16A-1P | CTT CTG CTT ACC ATA TTT GAC | SEQ ID NO.:13 |
| EX16A-2-Cy | TAAT ACA GAC ATA CTT AAC G | SEQ ID NO.:14 |
| EX-18-1-P | GG AGA AGG AGA AGG AAG AG T | SEQ ID NO.:15 |
| EX18-2-Cy | ATC TAT GAG AAG GAA AGA AGA | SEQ ID NO.:16 |
| Ex-19-1-Cy | GGC CAA ATG ACT GTC AAA GA | SEQ ID NO.:17 |
| Ex-19-2-P | TGC TTC AGG CTA CTG GGA TT | SEQ ID NO.:18 |

TABLE II mPCR Group II Primers:

| | | |
|---|---|---|
| Ex-3-1-Cy | C GGC GAT GTT TTT TCT GGA G | SEQ ID NO.:19 |
| Ex-3-2-P | T ACA AAT GAG ATC CTT ACC C | SEQ ID NO.:20 |
| Ex-4-1-P | AGC TTC CTA TGA CCC GGA TA | SEQ ID NO.:21 |
| Ex-4-2-Cy | TGT GAT GAA GGC CAA AAA TG | SEQ ID NO.:22 |
| EX-10-1-P | TGT TCT CAG TTT TCC TGG AT | SEQ ID NO.:23 |
| EX-10-2-Cy | CTC TTC TAG TTG GCA TGC TT | SEQ ID NO.:24 |
| Ex-11-1-P | CAG ATT GAG CAT ACT AAA AG | SEQ ID NO.:25 |
| EX11-2-Cy | AC ATG AAT GAC ATT TAC AGC | SEQ ID NO.:26 |
| Int-19-1-Cy | AA TCA TTC AGT GGG TAT AAG C | SEQ ID NO.:27 |
| Int-19-2-P | CCT CCT CCC TGA GAA TGT TGG | SEQ ID NO.:28 |
| EX-20-1-P | C TGG ATC AGG GAA GA GAA GG | SEQ ID NO.:29 |
| EX20-2-Cy | TCC TTT TGC TCA CCT GTG GT | SEQ ID NO.:30 |
| EX21-1-P | TGA TGG TAA GTA CAT GGG TG | SEQ ID NO.:31 |
| EX21-2-Cy | CAA AAG TAC CTG TTG CTC CA | SEQ ID NO.:32 |

| PCR Master mix composition For 20 μl reaction/sample: | |
| --- | --- |
| Components | Volume (μl) |
| 10X PCR buffer | 2.0 |
| 25 mM MgCl$_2$ | 1.4 |
| dNTPs (2.5 mM) | 4.0 |
| Primer mix (Multiplex 10x) | 3.0 |
| Taq DNA polymerase | 0.6 |
| ddH2O | 3.0 |
| DNA | 6.0 |
| Total | 20 |

| PCR Cycling Conditions | | |
| --- | --- | --- |
| Hot Start | | |
| 94° C. | 15 min | |
| 94° C. | 30 sec, 60% ramp | |
| 60° C. | 30 sec, 50% ramp | 30 cycles |
| 72° C. | 50 sec, 35% ramp | |
| 72° C. | 8 min | |

Amplifications were performed using a Perkin Elmer 9700 thermal cycler. Optimal primer concentrations were determined for each primer pair. The reaction volume can be adjusted according to experimental need.

Post PCR processing: Following amplification, PCR products were purified using either a QIAquick PCR purification kit (QIAGEN, Cat # 28104), or by Exonuclease 1 treatment (Amersham). For the latter procedure: an aliquot of 8 μl of PCR product was added in a clean tube with 2.5 μl of Exonuclease 1 (Amersham), incubated at 37° C. for 15 minutes and denatured at 80° C. for 15 min. Thereafter, single stranded DNA was generated as follows:

PCR reaction products were incubated with 2.5 units of λ exonuclease in 1× buffer at 37° C. for 20 min, followed by enzyme inactivation by heating to 75° C. for 10 min. Under these conditions, the enzyme digests one strand of duplex DNA from the 5'-phosphorylated end and releases 5'-phosphomononucleotides (J. W. Little, et al., 1967). Single-stranded targets also can be produced by other methods known in the art, although heating the PCR products to generate single stranded DNA, is undesirable. The single stranded DNA can be used directly in the assay.

ON CHIP Hybridization—The CFTR gene sequence from Genebank was used to model the wild-type. The 52 probes were divided into two groups on the basis of their sequence homologies, in accordance with the "heuristic" probe selection algorithm, i.e., in such a way as to avoid overlapping homologies among different probes to the extent possible. The mutations included in each group were selected so as to minimize overlap between probe sequences in any group and thereby to minimize intra-group cross-hybridization under multiplex assay conditions.

Probe sequences were designed by PRIMER 3.0 software (see The Broad Institute website, incorporated herein by reference), seeking to include the following characteristics in each probe:
(a) a mismatch in the center of the probe;
(b) probe length 16-21 bases;
(c) low self compatibility;
(d) 30-60% GC content; and
(e) no more than three consecutive identical bases.

Each probe sequence was aligned with its complementary exon sequence. See Baylor College of Medicine HGSC. BCM Search Launcher website incorporated herein by reference. The percent homology between each probe and non-desired target sequences (i.e., those sequences representing mutations other than those which the probe is intended to hybridize with) was calculated, and probes were selected such that the percent homology between probes for each mutation and non-desired target sequences on the same array was less than 50%.

Probe selection was further refined based on the heuristic selection algorithm, set forth above. Probe selection was also refined in part on experimental selection, and in part on consideration that certain mismatched base pairs, particularly, G-T, will tend to be stable. In instances where probes could hybridize incorrectly with mismatches forming a G-T pairing, and in certain other instances, the anti-sense probes were used, rather than the sense probes, if such stable mismatches could be avoided, or if it was experimentally demonstrated that incorrect hybridization was eliminated by using the anti-sense probe. The cases where antisense probes were used are indicated in the Probe Sequence Table III below.

Wild type and mutant probes for 26 CF mutations were synthesized with either 5' Biotin-TEG or amine modification at the 5' end (Integrated DNA Technologies). Different bead chemistry can use a different 5' end, such that a biotin modification is coupled to beads coated with neutravidin, and an amine modification is coupled to beads coated with BSA. Probes were dissolved in 1× TE or dsH$_2$O at a concentration of 100 μM. An aliquot of 100 μl of 1% bead solids, for each type of bead, was washed three times with 500 μl of TBS-1 (1× TE, 0.5 M NaCl2). Probes were added to 500 μl bead suspension and incubated at room temperature for 45-60 minutes on a roller. Beads were washed once with wash solution TBS-T (1× TE, 0.15 M NaCl$_2$, 0.05% TWEEN 20 (polysorbate detergent)) or PBS-T (Phosphate buffered saline, TWEEN 20 (polysorbate detergent)) and twice with TBS-2 (1× TE, 0.15 M NaCl$_2$) and re-suspended in 1× TBS-2. Beads were assembled on the surface of chips as described earlier. The probes were also divided into two groups and assembled on two separate chips. A third group was assembled for reflex test including 5T/7T/9T polymorphisms. Negative and positive controls were also included on the chip surface, and assay signal was normalized using these controls. For negative controls, beads were coupled with a 10-mer strand of dCTP (Oligo-C) and immobilized on the chip surface. For a positive control signal, the human β Actin sequence was used. The signal from Oligo-C was used as the background to subtract the noise level and β Actin was used to normalize the data.

TABLE IIIA

| Hybridization Group I: | |
| --- | --- |
| Bead cluster | Mutation |
| 1 | OLIGO-C(control) |
| 2 | BA |
| 3 | OligoC-1 |
| 4 | G85E-WT |
| 5 | G85E-M |
| 6 | 621+1G>T-WT |
| 7 | 621+1G>T-M |
| 8 | R117H-WT |
| 9 | R117H-M |
| 10 | I148-WT |
| 11 | I148-M |
| 12 | A455E-WT |
| 13 | A455E-M |

TABLE IIIA-continued

Hybridization Group I:

| Bead cluster | Mutation |
|---|---|
| 14 | 508-WT |
| 15 | OLIGOC-2 |
| 16 | F508 |
| 17 | I507 |
| 18 | G542-WT |
| 19 | G542-M |
| 20 | G551D-WT |
| 21 | G551D-M |
| 22 | R560-WT |
| 23 | R560-M |
| 24 | R553X-WT |
| 25 | R553X-M |
| 26 | OLIGOC-3 |
| 27 | 1717−1G>A-WT |
| 28 | 1717−1G>A-M |
| 29 | 3849+10kb-WT |
| 30 | 3849+10kb-M |
| 31 | W1282X-WT |
| 32 | OLIGOC-4 |
| 33 | W1282X-M |
| 34 | N1303K-WT |
| 35 | N1303K-M |
| 36 | OLIGOC-5 |

TABLE IIIB

Hybridization Group II

| Bead Cluster | Mutation |
|---|---|
| 1 | BA |
| 2 | 1898+5G-WT |
| 3 | OLIGO-C(control) |
| 4 | 1898+5G-M |
| 5 | OLIGO-C-1 |
| 6 | R334W-WT |
| 7 | R334W-M |
| 8 | 1898+1G>A-WT |
| 9 | 1898+1G>A-WT |
| 10 | 1078delT-M |

TABLE IIIB-continued

Hybridization Group II

| Bead Cluster | Mutation |
|---|---|
| 11 | OLIGO-C-2 |
| 12 | D1152-WT |
| 13 | D1152-M |
| 14 | R347P-WT |
| 15 | R347P-M |
| 16 | 711+1G>T-WT |
| 17 | 711+1G>T-M |
| 18 | 3659delC-WT |
| 19 | 3659delC-M |
| 20 | OLIGO-C-3 |
| 21 | R1162X-WT |
| 22 | R1162X-M |
| 23 | 2789+5G-WT |
| 24 | 2789+5G-M |
| 25 | 3120+1G>A-WT |
| 26 | 3120+1G>A-WT |
| 27 | OLIGO-C-4 |
| 28 | A455E-WT |
| 29 | A455E-M |
| 30 | 2184delA-WT |
| 31 | 2184delA-M |
| 32 | 1078delT-WT |
| 33 | OLIGO-C-5 |

TABLE IIIC

Hybridization Group III (total 6 groups)

| Cluster # | Mutation |
|---|---|
| 1 | β Actin |
| 1 | Oligo C |
| 2 | 5T |
| 3 | 7T |
| 4 | 9T |

Probe sequences for detecting each mutation were as follows (probes to sense or antisense sequences were selected as described above):

TABLE IV

| NORMAL/VARIANT SEQUENCE | CAPTURE PROBES | |
|---|---|---|
| EX-3 | AT GTT CTA TGG AAT CTT TT TA | SEQ ID NO.:33 |
| G85E | AT GTT CTA TGA AAT CTT TT TA | SEQ ID NO.:34 |
| EX-4 | TA TAA GAA GGT AAT ACT TC CT | SEQ ID NO.:35 |
| 621-M | TATAA GAA GTT AATACT TC CT | SEQ ID NO.:36 |
| INT-4 | CC TCA TCA CAT TGG AAT GC AG | SEQ ID NO.:37 |
| I148T | CC TCA TCA CAC TGG AAT GC AG | SEQ ID NO.:38 |
| EX-4 | CAA GGA GGA ACG CTC TAT CG C | SEQ ID NO.:39 |
| R117H | CAAGGA GGA ACA CTC TAT CGC | SEQ ID NO.:40 |
| EX-5 | ATG GGT ACA TAC TTC ATC AA A | SEQ ID NO.:41 |
| 711 + 1G | ATG GGT ACA TAA TTC ATC AAA | SEQ ID NO.:42 |
| EX-7 | GAA TAT TTT CCG GAG GAT GAT | SEQ ID NO.:43 |
| 334-M | GAA TAT TTT CCA GAG GAT GAT | SEQ ID NO.:44 |

TABLE IV-continued

| NORMAL/VARIANT SEQUENCE | CAPTURE PROBES | |
|---|---|---|
| EX-7 | CAT TGT TCT GCG CAT GGC GGT | SEQ ID NO.:45 |
| 347-M | CAT TGT TCT GCC CAT GGC GGT | SEQ ID NO.:46 |
| EX-7 | CT CAG GGT TCT TTG TGG TG TT | SEQ ID NO.:47 |
| 1078DEL T | CT CAG GGT TC TTG TGG TG TT | SEQ ID NO.:48 |
| EX-9 | ACA GTT GTT GGC GGT TGC TGG | SEQ ID NO.:49 |
| A455E | ACA GTT GTT GGA GGT TGC TGG | SEQ ID NO.:50 |
| EX-10 | AAA GAA AAT ATC ATC TTT GGT | SEQ ID NO.:51 |
| F508 | AAA GAA AAT ATC ATT GGT GT | SEQ ID NO.:52 |
| I507 | AAA GAA AAT ATC TTT GGT GT | SEQ ID NO.:53 |
| EX-12 | ATA TTT GAA AGG TAT GTT CT TT | SEQ ID NO.:54 |
| 1898 + 1 | ATA TTT GAA AGA TAT GTT CT TT | SEQ ID NO.:55 |
| Ex-13 | GAA ACA AAA AAA CAA TCT TTT | SEQ ID NO.:56 |
| 2184 delA | GAA ACA AAA AA CAA TCT TTT | SEQ ID NO.:57 |
| EX-14B | TTG GAA AGT GAG TAT TCC ATG | SEQ ID NO.:58 |
| 2789 + 5G | TTG GAA AGT GAA TAT TCC ATG | SEQ ID NO.:59 |
| EX-16 | ACT TCA TCC AGA TAT GTA AAA | SEQ ID NO.:60 |
| 31120 + 1G/A | ACT TCA TCC AGG TAT GTA AAA | SEQ ID NO.:61 |
| Ex-11 | TAT AGT TCT TGG AGA AGG TGG | SEQ ID NO.:62 |
| G542X | TAT AGT TCT TTG AGA AGG TGG | SEQ ID NO.:63 |
| EX-11 | TCT TTA GCA AGG TGA ATA ACT | SEQ ID NO.:64 |
| R560 | TCT TTA GCA ACG TGA ATA ACT | SEQ ID NO.:65 |
| EX-11-553/551 | GAG TGG AGG TCA ACG AGC AAG | SEQ ID NO.:66 |
| G551D | GAG TGG AGA TCA ACG AGC AAG | SEQ ID NO.:67 |
| R553X | GTG GAG GTC AAT GAG CAA GA | SEQ ID NO.:68 |
| EX-11 | TGG TAA TAG GAC ATC TCC AAG | SEQ ID NO.:69 |
| 1717-M | TGG TAA TAA GAC ATC TCC AAG | SEQ ID NO.:70 |
| EX-18 | ACT CCA GCA TAG ATG TGG ATA | SEQ ID NO.:71 |
| 1152X | ACT CCA GCA TAC ATG TGG ATA | SEQ ID NO.:72 |
| EX-19-SENSE | GAA CTG TGA GCC GAG TCT TTA | SEQ ID NO.:73 |
| R1162X | GAA CTG TGA GCT GAG TCT TTA | SEQ ID NO.:74 |
| EX-19 | TGG TTG ACT TGG TAG GTT TAG | SEQ ID NO.:75 |
| | 3659 TGG TTG ACT TG TAG GTT TAC | SEQ ID NO.:76 |
| INT-19 | T TAA AAT GGT GAG TAA GA CAC | SEQ ID NO.:77 |
| | 3849 T TAA AAT GGC GAG TAA GA CAC | SEQ ID NO.:78 |
| EX-20 | TGC AAC AGT GGA GGA AAG CCT | SEQ ID NO.:79 |
| 1282X | TGC AAC AGT GAA GGA AAG CCT | SEQ ID NO.:80 |
| EX-21 | A TTT AGA AAA AAC TTG GAT CC | SEQ ID NO.:81 |

TABLE IV-continued

| NORMAL/VARIANT SEQUENCE | CAPTURE PROBES | |
|---|---|---|
| N1303K | A TTT AGA AAA AAG TTG GAT CC | SEQ ID NO.:82 |
| β A-PROBE | AG GAC TCC ATG CCC AG | SEQ ID NO.:83 |

The hybridization buffer has been optimized for use in uniplex and/or multiplex hybridization assays and is composed of (final concentrations): 1.125 M Tetramethyl-Ammonium Chloride (TMAC), 18.75 mM Tris-HCL (pH 8.0), 0.75 mM EDTA (pH 8.0) and 0.0375% SDS. Ten µl of hybridization mixture containing buffer and ssDNA was added on the chip surface and incubated at 55° C. for 15 minutes. This is a shorter hybridization time than the several hours normally used, because longer hybridization times tend to generate uncontrolled excess hybridization. The chip was washed with 1× TMAC buffer three times, covered with a clean cover slip and analyzed using a BAS imaging system. Images are analyzed to determine the identity of each of the probes. The results are shown below in FIGS. 1 and 2.

Each allele of a given mutation was analyzed as follows. First, the signal from the hybridized alleles was corrected as follows:
  (i) Signal for allele A (labeled amplicon) =Raw signal from labeled amplicon-hybrid minus raw counts from negative (background) control
  (ii) Signal for allele B (unlabeled amplicon) =Raw signal from unlabeled amplicon-hybrid minus raw counts from negative (background) control Then an allelic ratio was calculated:
  Allelic ratio = Signal for allele A/Signal for allele B When the value of (i) was less than or equal to zero, it was adjusted to 0.01 to avoid the generation of negative values. Allelic ratios of >2 were scored as homozygous for allele A (indicating mutant/polymorph), while an allelic ratio of <0.5 was scored as homozygous for allele B (wild type). An allelic ratio of 0.8 to 1.2 was scored as heterozygous. Values which fell in between these thresholds were considered ambiguous and the assay was repeated.

EXAMPLE II

Screening of Multiple Patient Samples—Side-by-Side Comparison of hMAP with Dot Blot Analysis A number of patient samples were obtained and amplified for simultaneous screening. The method of amplification and primer design was as described above. After amplification, analysis techniques on samples were compared for 26 CFTR mutations. A set was analyzed using conventional dot blot hybridization methods, and the same set was analyzed with the methods and reagents of the invention. The results for each patient sample were compiled and both results were compared. There was 100% concordance with the two methods of detection. The number of samples identified as positives for each mutation are listed in Table V.

TABLE V

Comparison of Testing of Samples
Samples tested by dot-blot and methods described herein

| Mutations | # Positives | # Negatives | Total |
|---|---|---|---|
| G85E | 11 | 11 | 22 |
| G85E/621+1G | 8 | | 8 |
| 621+1G>T | 11 | 13 | 24 |
| 621+1G>T/delF508 | 2 | | 2 |
| R117H | 19 | | 19 |
| R117H/delF508 | 1 | | 1 |
| I148T | 48 | | 48 |
| delF508 | 58 | 14 | 72 |
| I507 | 11 | | 11 |
| delF508/R560 | 1 | | 1 |
| G542X | 44 | 11 | 55 |
| G551D | 11 | | 11 |
| R553X | 15 | | 15 |
| 1717-1G>A | 14 | | 14 |
| R560T | 9 | | 9 |
| 3849+10kbC>T | 25 | 14 | 39 |
| W1282X | 53 | 13 | 66 |
| N1303K | 31 | 15 | 46 |
| mPCR-WT | | 87 | 87 |
| 711+1G>T | 19 | 9 | 28 |
| 711+1G>T/621+1G | 1 | | 1 |
| R334W | 19 | 11 | 30 |
| R347P | 13 | | 13 |
| 1078delT | 11 | | 11 |
| A455E | 18 | 11 | 29 |
| 1898+1G>A | 24 | 10 | 34 |
| 2184delA | 10 | 10 | 20 |
| 2789+5G>A | 20 | 10 | 30 |
| 3120+1g>A | 18 | 10 | 28 |
| R1162X | 13 | 8 | 21 |
| 3569delC | 8 | | 8 |
| D1152 | 47 | 9 | 56 |
| mPCR-WT | | 80 | 80 |
| TOTAL | | | 939 |

It should be understood that the terms, expressions and examples described herein are exemplary only and not limiting and that processes and methods can be performed in any order, unless the sequence of steps is specified. The invention is defined only in the claims which follow and includes all equivalents of the claims.

What is claimed is:

1. A method of differentiating homozygous, heterozygous and wild-type alleles in a target sample comprising mutant or polymorphic alleles or wild-type alleles using results obtained from a probe array, wherein individual probes in the array are designed to detect designated mutant or polymorphic alleles or wild-type alleles through hybridization of said probes and targets, where the results compensate for hybridization between probes and targets other than their designated targets, comprising:

amplifying the genomic regions in the target sample that are predicted to include said mutant or polymorphic alleles or said wild-type alleles, thereby producing a first set of labeled amplicons having a region complementary to a subsequence of said mutant or polymorphic alleles (if said mutant or polymorphic alleles are present in said target sample) and a second set of labeled amplicons having a region complementary to a subsequence of said wild-type alleles (if said wild-type alleles are present in said target sample);

providing an array of probe pairs, the first member of each pair being complementary, in whole or in substantial part, to a subsequence of a first-set amplicon and the second member of each pair being complementary, in whole or in substantial part, to a subsequence of a second-set amplicon;

contacting under hybridizing conditions said array of probe pairs with said amplicons;

detecting hybridization between probes and said amplicon sets based on the presence of signals from the labeled, hybridized amplicons, said signals being corrected to adjust for hybridization between probes and amplicons other than their designated amplicons as follows:

(i) determining the intensity of signals from hybridization of first-set amplicons and from hybridization of second-set amplicons, as corrected for background signals, and (ii) determining the ratio of said signals, wherein the ratio of the intensity of first-set amplicon signals to the intensity of second-set amplicon signals is designated as a first ratio (a), and wherein the ratio of the intensity of second-set amplicon signals to the intensity of first-set amplicon signals is designated as second ratio (b); and defining three relative ranges of values for said ratios such that: (i) the lowest range of ratio (a) indicates that said target sample is homozygous for wild-type alleles and the lowest range of ratio (b) indicates that said target sample is homozygous for mutant or polymorphic alleles, (ii) a middle range of either ratio (a) or (b) indicates that said target sample is heterozygous, and (iii) the highest range of ratio (a) indicates that the said target sample is homozygous for mutant or polymorphic alleles and the highest range of ratio (b) indicates that said target sample is homozygous for wild-type alleles.

2. The method of claim 1 further including the step of generating single-stranded DNA from said amplicons.

3. The method of claim 2 further including the step of labeling one of the strands of either of said amplicon sets.

4. The method of claim 1 wherein said relative value ranges are defined such that: >2 indicates that said target sample is homozygous for mutant or polymorphic alleles, <0.5 indicates that said target sample is homozygous for wild-type alleles and 0.8 to 1.2 indicates that said target sample is heterozygous.

* * * * *

UNITED STATES PATENT AND TRADEMARK OFFICE
CERTIFICATE OF CORRECTION

PATENT NO. : 7,501,266 B2  
APPLICATION NO. : 11/439697  
DATED : March 10, 2009  
INVENTOR(S) : Ghazala Hashmi and Michael Seul Page 1 of 1

It is certified that error appears in the above-identified patent and that said Letters Patent is hereby corrected as shown below:

Claim 1, Column 52, line 2, delete ", in whole or in substantial part," and insert --subsequence--.

Claim 1, Column 52, line 71 and 72, delete ", in whole or in substantial part," and insert --subsequence--.

Claim 4, Column 54, line 9, after <0.5 please insert --, but greater than 0,--.

Signed and Sealed this  
Twenty-eighth Day of June, 2011

David J. Kappos  
*Director of the United States Patent and Trademark Office*